United States Patent [19]

Sekihachi et al.

[11] Patent Number: 5,286,881
[45] Date of Patent: Feb. 15, 1994

[54] PROCESS FOR PRODUCING BENZODIFURANONE COMPOUNDS USEFUL FOR DYEING OR PRINTING HYDROPHOBIC FIBER MATERIALS

[75] Inventors: Junichi Sekihachi; Jun Yamamoto, both of Osaka; Yutaka Kayane, Nara, all of Japan

[73] Assignee: Sumitomo Chemical Company Limited, Osaka, Japan

[21] Appl. No.: 953,767

[22] Filed: Sep. 30, 1992

Related U.S. Application Data

[63] Continuation of Ser. No. 639,089, Jan. 9, 1991, abandoned.

[30] Foreign Application Priority Data

Jan. 12, 1990 [JP] Japan ..................... 2-5223

[51] Int. Cl.$^5$ ............. C07D 307/91; C07D 495/02; C07D 403/12; C07D 405/12
[52] U.S. Cl. .................... 549/299; 549/50; 549/51; 549/52; 549/57; 549/58; 549/60; 540/596; 546/197; 546/270; 544/60; 544/147; 544/148; 544/180; 544/212; 544/216; 544/375; 544/378; 548/128; 548/129; 548/159; 548/186; 548/193; 548/194; 548/200; 548/203; 548/225; 548/228; 548/229; 548/221; 548/222; 548/217; 548/233; 548/235; 548/526; 548/311.7; 548/305.1; 548/361.5; 548/362.1; 548/362.5; 548/364.4
[58] Field of Search ............... 546/270; 549/60, 299; 548/327, 336, 526; 540/596; 544/180, 212, 147, 375

[56] References Cited

U.S. PATENT DOCUMENTS

| | | | |
|---|---|---|---|
| 4,115,404 | 9/1978 | Greenhalgh et al. | 549/299 |
| 4,122,087 | 10/1978 | Greenhalgh et al. | 548/433 |
| 4,333,877 | 6/1982 | Carey et al. | 549/299 |
| 4,650,882 | 3/1987 | Kenyon et al. | 549/299 |
| 4,680,417 | 7/1987 | Kenyon et al. | 549/299 |
| 4,916,240 | 4/1990 | Kenyon | 549/299 |
| 5,223,616 | 6/1993 | Yamamoto et al. | 544/153 |

FOREIGN PATENT DOCUMENTS

| | | |
|---|---|---|
| 146269 | 6/1985 | European Pat. Off. |
| 252406 | 1/1986 | European Pat. Off. |
| 0294029 | 12/1988 | European Pat. Off. |
| 0305886 | 3/1989 | European Pat. Off. |
| 0363034 | 4/1990 | European Pat. Off. ............ 549/299 |
| 0371223 | 6/1990 | European Pat. Off. ............ 549/299 |
| 1-258677 | 10/1989 | Japan ............................... 549/299 |
| 2068402 | 8/1981 | United Kingdom |
| 2103231 | 2/1983 | United Kingdom ............... 549/299 |

OTHER PUBLICATIONS

112 Chemical Abstracts No. 22—Abstract No. 200605u (May 28, 1990).
C. W. Greenhalgh et al, The Synthesis of Quinodimethanes In The Benzodifuranone And Benzodipyrrolidone Series, 1 Dyes and Pigments 103-120 (1980).

*Primary Examiner*—C. Warren Ivy
*Assistant Examiner*—A. A. Owens
*Attorney, Agent, or Firm*—Cushman, Darby & Cushman

[57] ABSTRACT

A benzodifuranone compounds of the formula,

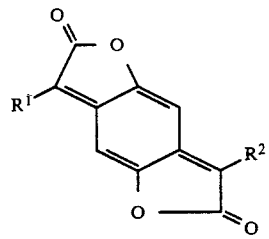

wherein $R^1$ and $R^2$ are each independently a naphthyl group or an unsubstituted or substituted phenyl group, which is useful for dyeing or printing hydrophobic fiber materials, is prepared in high purity and high yield by allowing benzofuran compounds of the formula, (Abstract continued on next page.)

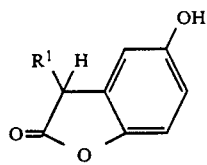
wherein $R^1$ is as defined above, to react with acetonitrile compounds of the formula,
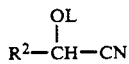
wherein $R^2$ is as defined above, and then carrying out an oxidation reaction to give the benzodifuranone compound.
16 Claims, No Drawings

PROCESS FOR PRODUCING BENZODIFURANONE COMPOUNDS USEFUL FOR DYEING OR PRINTING HYDROPHOBIC FIBER MATERIALS

This is a continuation of application Ser. No. 07/639,089, filed on Jan. 9, 1991 now abandoned.

The present invention relates to a process for producing benzodifuranone compounds. More specifically, the present invention relates to a process for producing benzodifuranone compounds useful for dyeing or printing hydrophobic fiber materials, for example, polyester fibers or fiber materials containing the same, in a red color.

Various benzodifuranone compounds useful for dyeing or printing hydrophobic fiber materials and a method for preparing the same are mentioned in, for example, JP 61-54058, 1-258677 and 1-36859. In addition, a process using a mandelic acid compound as one of starting materials and a process using phenylglyoxylic acid compounds as one of staring materials are proposed (JP 60-178889 and European Patent Application No. 252,406).

However, these known processes all are not satisfactory yet from an economical point of view.

The present inventors have made extensive study to find a process for commercially producing benzodifuranone compounds. As a result, the present invention is attained.

The present invention provides a process for producing compounds of the following formula (I),

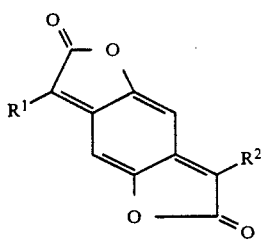
(I)

wherein $R^1$ and $R^2$ are each independently a naphthyl group or an unsubstituted or substituted phenyl group, which comprises allowing benzofuran compounds of the following formula (II),

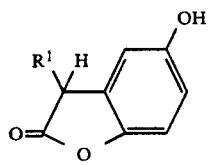
(II)

wherein $R^1$ is as defined above, to react with acetonitrile compounds of the following formula (III),

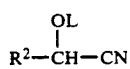
(III)

$$R^2-\underset{\underset{L}{|}}{CH}-CN$$

wherein $R^2$ is as defined above, L is $-COR^3$, $-CO_2R^4$ or $-SO_2R^5$ in which $R^3$, $R^4$ and $R^5$ are each independently an alkyl or a phenyl group, followed by oxidation. The present invention provides also a process for dyeing or printing hydrophobic fiber materials or fiber materials containing the same, with the benzodifuranone compounds of the formula (I).

In the above formula (I), the phenyl represented by $R^1$ and/or $R^2$ includes a phenyl group substituted or not substituted by at least one of the groups of nitro, halo, alkyl, alkoxyl, phenyl, alkoxyphenyl, phenoxy, hydroxyl, cyano, carboxyl, alkoxycarbonyl, phenoxycarbonyl, carbamoyl, sulfo, chlorosulfonyl, alkoxysulfonyl, phenoxysulfonyl, sulfamoyl, mercapto, alkylthio, phenylthio, amino, alkylamino, acylamino, phospho, alkylphosphonyl, phenylphosphonyl, alkylsulfonyl, phenylsulfonyl, formyl, azo and a group represented by the formula (i) or (ii);

(i)

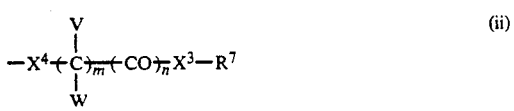
(ii)

wherein $R^6$ is a methylene group or a straight or branched $C_2$-$C_6$ alkylene group which may be substituted by hydroxyl group, an alkoxyl group or an alkylcarbonyloxy group, $X^1$ is a direct linkage or a divalent group of $-O-$, $-S-$, $-SO-$, $-SO_2-$,

in which $R^8$ is a hydrogen atom or an alkyl group,

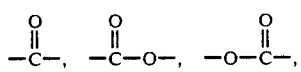

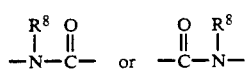

in which $R^8$ is as defined above, $X^2$ is $-O-$ or

in which $R^8$ is as defined above, T and U are each independently a hydrogen atom or an alkyl group, l is 0 or an integer of 1 to 3, Q is an unsubstituted or substituted 5-, 6- or 7-membered saturated or unsaturated heterocyclic residue, $R^7$ is an alkyl group, $X^3$ is $-O-$ or $-S-$, $X^4$ is $-O-$ or

in which $R^8$ is as defined above, V and W are each independently a hydrogen atom or an alkyl group, m is an integer of 1 to 3, n is 0 or 1, provided that m+n is at least 2.

In the substituents optionally appended to the phenyl group represented by $R^1$ and/or $R^2$, the alkyl, alkoxyl and their moieties in the alkylamino, alkylthio, alkylsulfonyl, alkylphosphonyl, alkoxycarbonyl, alkylsulfonyl and alkylphenyl groups are those having 1 to 4 carbon atoms. Furthermore, they may further be substituted by a halo group such as chloro, bromo, fluoro, etc., a $C_1$-$C_4$ alkoxyl group, a phenyl group, a $C_1$-$C_4$ alkoxyphenyl group, a phenoxy group, a hydroxyl group or a cyano group.

The phenyl and phenyl moiety in the phenoxy, phenoxycarbonyl, phenoxysulfonyl, phenylphosphonyl and phenylthio groups, which are optionally appended to the phenyl group may be substituted or not substituted by a halo group such as chloro, bromo, fluoro, etc. and a nitro group.

The acylamino group includes a formylamino group, a $C_1$-$C_4$ acylamino group such as an acetylamino group, a propionylamino group, a butyrylamino group, a valerylamino group, an acryloylamino group and a benzoylamino group.

The unsaturated heterocyclic residue represented by Q includes groups of furyl, thienyl, pyrrolyl, pyridyl, pyranyl, thiazolyl, oxazolyl, pyrazolyl, imidazolyl, thiadiazolyl and s-triazoyl, which are represented by the following formulas, respectively.

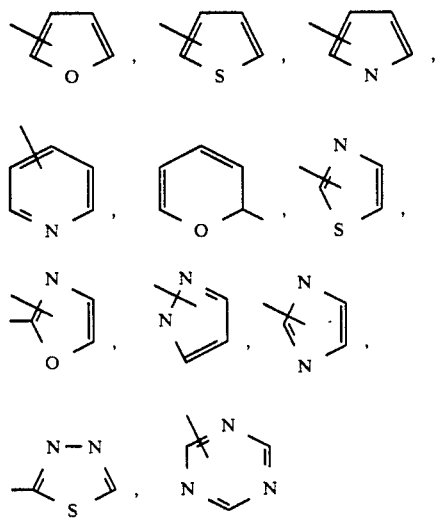

The saturated heterocyclic residue represented by Q includes those represented by the following formulas.

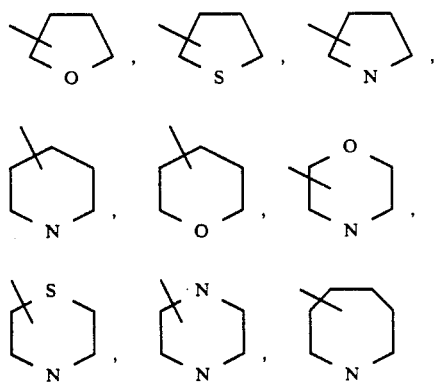

Of these, preferred are groups of tetrahydrofuryl, tetrahydrothienyl, pyrrolidyl, piperidyl, tetrahydropyranyl, piperazinyl, morpholinyl and hexahydroazepinyl, and particularly preferred are tetrahydrofuryl, pyrrolidyl, piperidyl, tetrahydropyranyl and morpholinyl.

The heterocyclic residue in the present invention may be condensed with benzene or heterocyclic ring to form those exemplified below.

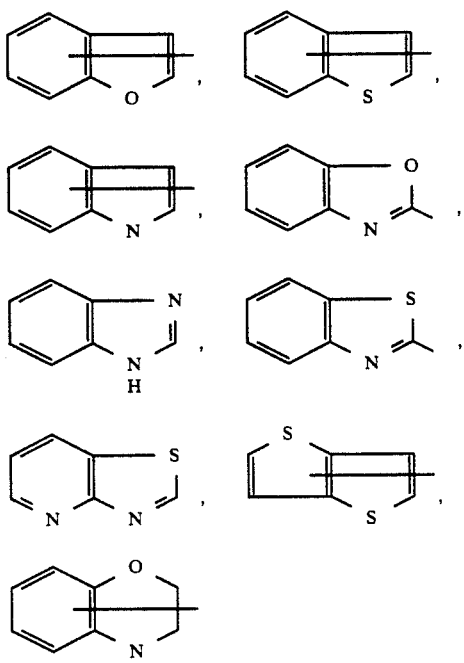

Among them, preferred are those condensed with benzene ring such as benzofuranyl, benzothienyl, indolyl, benzoxazolyl, benzoimidazolyl and benzothiazolyl.

The hetrocyclic residue described above is unsubstituted or substituted by one or two halo groups as fluoro, chloro and bromo, hydroxyl, $C_1$-$C_4$ alkyl, $C_1$-$C_4$ alkoxyl, $C_1$-$C_4$ alkylcarbonyl, $C_1$-$C_4$ alkoxycarbonyl, cyano, primary, secondary or tertiary amine unsubstituted or substituted by a $C_1$-$C_4$ alkyl or keto group.

The benzofuran compounds of the formula (II) mentioned in, for example, JP 60-178889 and European Patent Application No. 252406 are prepared by allowing hydroquinone to react with glycolic acid compounds of the following formula (IV),

wherein $R^1$ is as defined above.

The reaction between the hydroquinone glycolic acid compounds is carried out preferably in 73% sulfuric acid or a mixture of sulfuric acid and sulfuric acid or a mixture of sulfuric acid and acetic acid [Britrzzcki and Flateau, Ber., 30, 124 1897)].

The acetonitrile compounds of the formula (III) are prepared by allowing aldehyde compounds of the following formula (V),

wherein $R^2$ is as defined above, to react with metallic cyanide compounds such as potassium cyanide, sodium cyanide and the like in the presence of acid halides represented by the following formula (VI),

wherein L is as defined above and Hal is a halo group.

The symbol L in the formulas (III) and (VI) are preferably an alkylcarbonyl group such as acetyl, ethylcarbonyl, n- or iso-propylcarbonyl, n-, iso- or tert-butylcarbonyl and the like, a phenylcarbonyl group such as benzoyl, o-, m- or p-methylbenzoyl, o-, m- or p-methoxybenzoyl, o-, m- or p-nitrobenzoyl and the like, an alkoxycarbonyl group such as methoxycarbonyl, ethoxycarbonyl, n- or iso-propoxycarbonyl, n-, iso- or tert-butoxycarbonyl and the like, a phenoxycarbonyl group such as benzeneoxycarbonyl, p-methylbenzeneoxycarbonyl, p-nitrobenzeneoxycarbonyl and the like, an alkanesulfonyl group such as methanesulfonyl, ethanesulfonyl, n- or iso-propanesulfonyl, n- or iso-butanesulfonyl and the like, a phenylsulfonyl group such as benzenesulfonyl, p-methylbenzenesulfonyl, 4-methyl-2-nitrobenzenesulfonyl and the like.

A reaction between the benzofuran compounds (II) and the acetonitrile compounds (III) is carried out stoichiometrically in the presence or absence, preferably in the presence of a solvent, at a temperature ranging from 30° to 180° C., preferably from 50° to 120° C. The solvents usable for the reaction are hydrocarbons and halogenated hydrocarbons such as benzene, toluene, xylene, mesitylene, mono-, di- and tri-chlorobenzene, bromobenzene, chloronaphthalene, 1,2-dichloroethane, 1,1,1-trichloroethane, 1,1,2,2-tetrachloroethane, trichloroethylene, tetrachloroethylene, dichloromethane, chloroform, carbon tetrachloride, bromoform and low boiling petroleum fractions; nitrated hydrocarbons such as nitrobenzene, nitrotoluene and nitromethane; ketones such as methylisobutyl ketone and sulfolane; alkane carboxylic acids and their anhydrides such as formic acid, acetic acid, propionic acid and acetic anhydride. Among them, preferable are aromatic hydrocarbons and halogenated hydrocarbons such as toluene, monochlorbenzene, dichlorobenzene, 1,2-dichloroethane, 1,1,1-trichloroethane, 1,1,2,2-tetrachloroethane, trichloroethylene, dichloromethane and chloroform.

The reaction between (II) and (III) is advantageously carried out in the presence of acid catalysts. Examples of the acid catalysts are unsubstituted or substituted benzenesulfonic acids such as benzenesulfonic acid, p-toluenesulfonic acid and benzene-m-disulfonic acid; alkanesulfonic acids such as methanesulfonic acid; halogenated lower carboxylic acids such as trifluoroacetic acid; Lewis acids such as titanium tetrachloride, aluminum chloride, stannous chloride, stannic chloride, ferrous chloride, ferric chloride, zinc chloride and boron fluoride; mineral acids such as sulfuric acid and hydrochloric acid. Any amount of the acid catalysts may be used, but preferably, 0.5 mole or more, more preferably 0.8 to 2 moles, most preferably 0.9 to 1.5 moles per mole of the benzofuran compounds (II).

A product produced by the reaction between the benzofuran compounds (II) and the acetonitrile compounds (III) may be isolated, if desired. In the present invention, the product is subjected to a successive oxidation reaction, without the isolation.

The oxidation reaction is carried out preferably in the presence of a solvent at a temperature ranging from 30° to 180° C., preferably from 40° to 100° C. The solvent usable for the reaction between (II) and (III) mentioned above are also used in the oxidation reaction. In order to promote the oxidation reaction, oxidizing agents are preferably used. Examples of the oxidizing agents are chloranil, bromanil, thiosulfate, nitrite, hypochlorite, chlorite, chlorate, perchlorate, persulfate, periodate, perborate, permanganate, vanadate, dichromate, iodine, nitrate, tetrachlorohydroquinone, lead dioxide, manganese dioxide, vanadium pentoxide, nitrobenzene, dicyanodichlorobenzoquinone, hydrogen peroxide and air. They may be alone or in a mixture thereof, preferably a mixture of two or more. More preferred is a mixture of one nitrite with one selected from chloranil, bromanil and dicyanodichlorobenzoquinone. Particularly preferred is a mixture of sodium nitrite with chloranil. The oxidizing agent is used in a stoichiometric amount or more.

After the oxidation reaction is over, the desired benzodifuranone compounds of the formula (I) are isolated from the reaction mixture in a conventional manner. For instance, a hydrophilic solvent such as lower alkanol is added to the reaction mixture in order to precipitate the desired reaction product, followed by filtration.

The benzodifuranone compounds of the formula (I) are useful as disperse dyes for dyeing or printing hydrophobic fiber materials such as polyester fiber materials, triacetate fiber materials, diacetate fiber materials and polyacetate fiber materials, particularly polyester fiber materials.

Dyeing is conducted in such a manner that the benzodifuranone compounds are finely pulverized in an aqueous medium with the aid of naphthalenesulfonic acid/formaldehyde condensate, lignin sulfonic acid or the like, thereby obtaining a liquid dye dispersion. The liquid dye dispersion may be used as it is or dried with, for example, spray driers to the powdery form. The dyeing is carried out, for example, by a high temperature dyeing method wherein the hydrophobic fiber materials are dipped in an aqueous dye bath, followed by heating to a temperature of 105° C. or higher, preferably 110° to 140° C. under increased pressures for 30 to 60 minutes. Another dyeing method is a carrier dyeing method wherein the dyeing is carried out in the presence of carriers such as o-phenylphenol, methylnaphthalene and the like at a relatively high temperature, for example, water-boiling temperature. Another is a thermosol method wherein the fiber materials are padded with an aqueous dye dispersion and dry-heated at a temperature of 100° C. or higher.

Printing is carried out by mixing the aqueous dye dispersion with suitable stock pastes to obtain a color past, printing the fiber materials with the color pasts and then steaming or thermosol-treating the printed fiber materials.

The process in accordance with the present invention gives the desired benzodifuranone compound in high purity and high yield using easily available starting materials without difficulty of recovery of the solvent, if used.

The present invention is explained in more detail with reference to the following examples, which are only illustrative but not limitative for the scope of the present invention. In the following examples, parts and % are by weight, unless otherwise defined.

EXAMPLE 1

1-Benzoyloxy-1-(p-tetrahydrofurfuryloxyphenyl)acetonitrile (3.37 parts), 5-hydroxy-2-oxo-3 phenyl-2,3-dihydrobenzofuran (2.26 parts), p-toluenesulfonic acid (2.06 parts) and water (0.22 part) were added to monochlorobenzene (33 parts), and thereafter, the mixture was kept at 80° C. for 5 hours. Then, chloranil (2.46 parts) was added to the reaction mixture. The resulting mixture was kept at 80° C. for additional 1 hour, therafter cooled to room temperature, and then mixed with methanol (30 parts), and stirred for 1 hour under ice-cooling.

The crystals produced were collected on a filter, washed with methanol (150 parts) and water (30 parts), and then dried to obtain a compound represented by the following formula (1) in high purity and high yield.

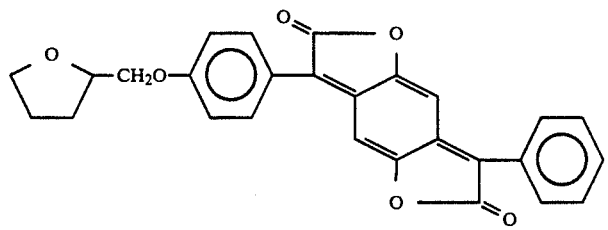

λmax 503 nm (dimethylformamide)

EXAMPLE 2

2-Ethoxycarbonyloxy-1-(p-tetrahydrofurfuryl-3-phenyl-2,3 dihydrobenzofuran (2.26 parts), p-toleune-sulfonic acid (2.06 parts) and water (0.22 part) were added to monochlorobenzene (33 parts), and thereafter, the mixture was kept at 75° C. for 4 hours. Then, chloranil (2.46 parts) was added to the reaction mixture. The resulting mixture was kept at 75° C. for additional 1.5 hours, therafter cooled to room temperature, and then mixed with methanol (35 parts), and stirred for 1 hour under ice-cooling.

The crystals produced were collected on a filter, washed with methanol (150 parts) and water (25 parts), and then dried to obtain a compound represented by the formula (1) in high purity and high yield.

EXAMPLE 3

1-Benzoyloxy-1-[p-(3-ethoxypropoxy)phenyl-]acetonitrile (3.40 parts), 5-hydroxy-2-oxo-3-phenyl-2,3-dihydrobenzofuran (2.26 parts), p-toluenesulfonic acid (2.06 parts) and water (0.22 part) were added to mono-chlorobenzene (30 parts), and thereafter, the mixture was kept at 85° C. for 5 hours. Then, chloranil (2.46 parts) was added to the reaction mixture. The resulting mixture was kept at 85° C. for additional 1 hour, thereafter cooled to room temperature, and then mixed with methanol (30 parts), and stirred for 1 hour under ice-cooling.

The crystals produced were collected on a filter, washed with methanol (140 parts) and water (35 parts), and then dried to obtain a compound represented by the following formula (2) in high purity and high yield.

chlorobenzene (35 parts). and thereafter, the mixture was kept at 80° C. for 5 hours. Then, chloranil (0.24 part) and sodium nitrite (0.62 part) were added to the reaction mixture. The resulting mixture was kept at 80° C. for additional 2 hours, thereafter cooled to room temperature, and then mixed with methanol (30 parts), and stirred for 1 hour under ice-cooling. The crystals produced were collected on a filter, washed with methanol (100 parts) and water (30 parts), and then dried to obtain a compound represented by the formula (1) in high purity and high yield.

EXAMPLES 5 to 19

Procedure of Example 1 was repeated, provided that the respective solvents as shown in the Table 1 were used in place of the monochlorobenzene used in Example 1 and the reactions between 1 benzoyloxy-1-(p-tetrahydrofurfuryloxyphenyl)-acetonitrile and 5-hydroxy-2-oxo-3-phenyl-2,3-dihyrobenzofuran were carried out at the respective temperatures as shown in the Table 1, thereby obtaining the compound represented by the formula (1) in high purity and high yield.

TABLE 1

| Example No. | Solvent | Amount (parts) | Temperature (°C.) |
|---|---|---|---|
| 5 | Benzene | 26.4 | 80 |
| 6 | Toluene | 26.0 | 80 |
| 7 | p-Xylene | 25.8 | 80 |
| 8 | o-Dichlorobenzene | 39.2 | 80 |
| 9 | Bromobenzene | 44.9 | 80 |
| 10 | Chloronaphthalene | 35.8 | 110 |
| 11 | 1,2-Dichloroethane | 37.7 | 80 |
| 12 | 1,1,1-Trichloroethane | 40.1 | 75 |
| 13 | 1,1,2,2-Tetrachloroethane | 47.6 | 80 |
| 14 | Trichloroethylene | 43.9 | 80 |
| 15 | Dichloromethane | 39.8 | 40 |
| 16 | Chloroform | 44.8 | 60 |
| 17 | Nitrobenzene | 35.9 | 90 |
| 18 | Methylisobutyl ketone | 24.0 | 85 |
| 19 | Acetic acid | 31.5 | 80 |

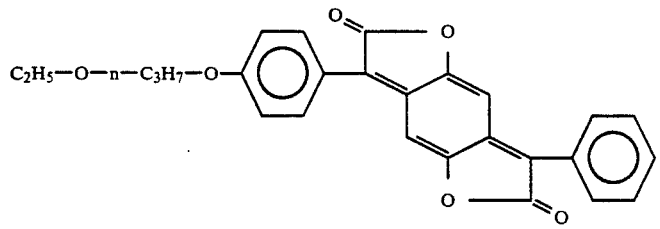

EXAMPLE 4

1-Benzoyloxy-1-(p-tetrahydrofurfuryloxyphenyl-)acetonitrile (3.37 parts), 5-hydroxy-2-oxo-3-phenyl-2,3-dihydrobenzofuran (2.26 parts), p-toluenesulfonic acid (2.06 parts) and water (0.22 part) were added to mono-

EXAMPLES 20 to 35

Procedure of Example 1 was repeated, provided that the reactions between 1-benzoyloxy-1-(p-tetrahydro furfuryloxyphenyl)-acetonitrile and 5-hydroxy-2-oxo-3- phenyl-2,3-dihydrobenzofuran were carried out using the respective oxidizing agents as shown in the Table 2 in place of the chloranil used in Example 1, thereby obtaining the compound represented by the formula (1) in high purity and high yield.

TABLE 2

| Example No. | Oxidizing agent | Amount (parts) |
|---|---|---|
| 20 | Sodium thiosulfate | 2.48 |
| 21 | Sodium nitrite | 0.69 |
| 22 | 10% Sodium hypochlorite | 7.60 |
| 23 | 10% Potassium hypochlorite | 9.00 |
| 24 | Sodium chlorite | 0.90 |
| 25 | Potassium chlorate | 1.22 |
| 26 | Sodium perchlorate | 1.22 |
| 27 | Ammonium persulfate | 2.28 |
| 28 | Sodium persulfate | 2.38 |
| 29 | Sodium periodate | 2.14 |
| 30 | Potassium permanganate | 1.58 |
| 31 | Nitrobenzene | 1.23 |
| 32 | Dicyanodichlorobenzoquinone | 1.54 |
| 33 | 30% Hydrogen peroxide | 1.13 |
| 34 | Ammonium metavanadate and air | 0.12 |
| 35 | 70% Nitric acid | 0.90 |

EXAMPLES 36 to 46

Procedure of Example 1 was repeated, provided that the respective acid catalysts as shown in the Table 3 were used in place of the p-toluenesulfonic acid used in Example 1 and the reactions between 1-benzoyloxy-1-(p-tetrahydrofurfuryloxyphenyl)-acetonitrile and 5-hydroxy-2-oxo-3-phenyl-2,3-dihydrobenzofuran were carried out at the respective temperatures as shown in the Table 3, thereby obtaining the compound represented by the formula (1) in high purity and high yield.

TABLE 3

| Example No. | Acid catalyst | Amount (parts) | Temperature (°C.) |
|---|---|---|---|
| 36 | Benzenesulfonic acid | 2.11 | 75 |
| 37 | Benzene-m-disulfonic acid | 2.91 | 65 |
| 38 | Methanesulfonic acid | 1.15 | 95 |
| 39 | Trifluoroacetic acid | 1.37 | 50 |
| 40 | Titanium tetrachloride | 2.27 | 70 |
| 41 | Aluminum chloride | 1.32 | 85 |
| 42 | Stannous chloride | 1.89 | 80 |
| 43 | Ferric chloride | 1.61 | 75 |
| 44 | Boron fluoride (etherate) | 1.14 | 120 |
| 45 | Sulfuric acid | 1.18 | 100 |
| 46 | Hydrochloric acid | 1.06 | 90 |

EXAMPLES 47 to 50

Procedure of Example 1 was repeated, provided that the reactions between 1-benzoyloxy-1-(p-tetrahydrofurfuryloxyphenyl)-acetonitrile and 5-hydroxy-2-oxo-3-phenyl-2,3-dihydrobenzofuran were carried out using the respective amount of p-toluenesulfonic acid as shown in the Table 4 in place of the p-toluenesulfonic acid (2.06 parts) used in Example 1, until the compound represented by the formula (1) was obtained in high purity and high yield.

TABLE 4

| Example No. | Amount of p-toluenesulfonic acid (parts) |
|---|---|
| 47 | 1.38 |
| 48 | 1.72 |
| 49 | 2.58 |
| 50 | 3.44 |

EXAMPLES 51 to 55

Procedure of Example 4 was repeated, provided that the reactions between 1-benzoyloxy-1-(p-tetrahydrofurfuryloxyphenyl)-acetonitrile and 5-hydroxy-2-oxo-3-phenyl-2,3-dihydrobenzofuran were carried out using the respective amount of chloranil and sodium nitrite as shown in the Table 5 in place of the chloranil (0.24 part) and sodium nitrite (0.62 part) used in Example 4, whereby obtaining the compound represented by the formula (1) in high purity and high yield.

TABLE 5

| Example No. | Chloranil (parts) | Sodium nitrite (part) |
|---|---|---|
| 51 | 0.025 | 0.68 |
| 52 | 0.12 | 0.66 |
| 53 | 0.50 | 0.55 |
| 54 | 0.74 | 0.48 |
| 55 | 1.48 | 0.28 |

EXAMPLES 56 to 68

Procedure of Example 1 was repeated, provided that the respective compounds represented by the formula (III) as shown in the Table 6 were used in place of the 1-benzoyloxy-1-(p-tetrahydrofurfuryloxyphenyl)-acetonitrile (3.37 parts) used in Example 1, until the compound represented by the formula (1) was obtained in high purity and high yield.

TABLE 6

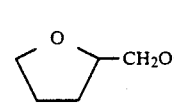

formula (III)

| Example No. | $R^9$ | Amount (parts) |
|---|---|---|
| 56 | 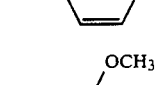 | 3.51 |
| 57 | 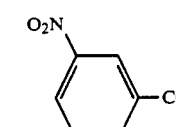 | 3.67 |
| 58 | 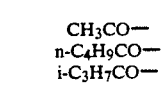 | 3.82 |
| 59 | $CH_3CO-$ | 2.75 |
| 60 | $n-C_4H_9CO-$ | 3.17 |
| 61 | $i-C_3H_7CO-$ | 3.03 |
| 62 | $CH_3OCO-$ | 2.91 |
| 63 | $i-C_4H_9OCO-$ | 3.33 |
| 64 | 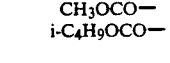 | 3.53 |
| 65 | $CH_3SO_2-$ | 3.11 |
| 66 | $C_2H_5SO_2-$ | 3.25 |
| 67 | $n-C_4H_9SO_2-$ | 3.53 |

TABLE 6-continued

| | |
|---|---|
| 68 | 3.87 | corresponding compounds represented by the formula III-a as shown in the Table 7 to react with 5-hydroxy-2-oxo-3-phenyl-2,3-dihydrobenzofuran.

TABLE 7

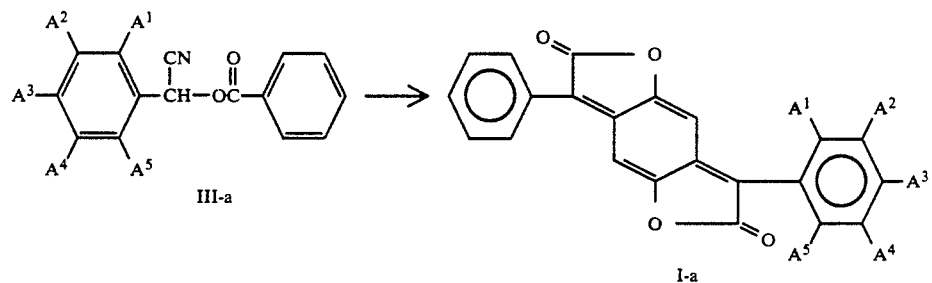

III-a → I-a

| Example No. | $A^1$ | $A^2$ | $A^3$ | $A^4$ | $A^5$ |
|---|---|---|---|---|---|
| 69 | H | H | n-C$_3$H$_7$O— | H | H |
| 70 | H | H | —O—CH(OCH$_3$)—CH$_2$OCH$_3$ | H | H |
| 71 | Cl | H | H | H | H |
| 72 | H | CH$_3$O— | HO— | CH$_3$O— | H |
| 73 | H | H | i-C$_4$H$_9$— | H | H |
| 74 | H | H | HO— | H | H |
| 75 | H | H | CH$_3$O—C$_6$H$_4$— | H | H |
| 76 | H | H | (CH$_3$)$_2$N—C$_6$H$_4$—N=N— | H | H |
| 77 | H | C$_2$H$_5$NHCO— | n-C$_3$H$_7$S— | H | H |
| 78 | H | CH$_3$—C$_6$H$_4$—OSO$_2$— | NH$_2$ | H | H |
| 79 | H | CH$_3$SO$_2$— | H | H | H |
| 80 | H | —CH$_3$ | —NH$_2$ | H | H |
| 81 | H | —OCH$_3$ | —NHC$_2$H$_5$ | H | H |
| 82 | H | —CH$_3$ | —NHCH$_2$-(tetrahydrofuran-2-yl) | H | H |

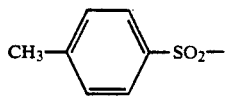

EXAMPLES 69 to 82

In a manner similar to that of Example 1, the respective compounds represented by the formula I-a were obtained in high purity and high yield by allowing the

EXAMPLES 83 to 89

In a manner similar to that of Example 1, the respective compounds represented by the formula I-b were obtained in high purity and high yield by allowing the corresponding compounds represented by the formula III-b as shown in the Table 8 to react with 5-hydroxy-2-oxo-3-phenyl-2,3-dihydrobenzofuran.

TABLE 8

Q¹—X—Q²—O—[phenyl with A]—CH(CN)—O—C(O)—[phenyl]   III-b

→

[structure I-b: diketo-quinoid system with A-substituted phenyl—O—Q²—X—Q¹]

| Example No. | A | Q² | X | Q¹ |
|---|---|---|---|---|
| 83 | H | —CH₂— | direct linkage | tetrahydropyran-2-yl (O in ring) |
| 84 | H | —CH₂CH₂CH₂— | " | tetrahydrofuran-2-yl |
| 85 | H | —(CH₂)₃CHCH₂— (with CH₃ branch) | " | morpholino (—N⌒O) |
| 86 | CH₃O— | —CH₂— | " | 5-methyl-tetrahydrothiophen-2-yl (S, CH₃) |
| 87 | H | —CH₂CH₂— | —S— | 6-chloro-benzothiazol-2-yl |
| 88 | CH₃— | —CH₂CH₂— | —NH— | pyrrolidin-2-yl (NH) |
| 89 | H | —CH₂CH₂CH₂— | —O— | —CH₂-(tetrahydrofuran-2-yl) |

EXAMPLE 90

The compound (1.0 part) represented by the formula (1) obtained in Example 1 was finely dispersed in an aqueous medium with the aid of naphthalenesulfonic acid/formaldehyde condensate (3.0 parts). The resulting dye dispersion was dried to powder form.

Polyesther cloth (10 parts, Tetron jersey, a product of Teijin Limited, Japan) was dipped in a dyebath containing the powder obtained (0.6 part), and dyeing was continued for 60 minutes at 130° to 135° C. under increased pressures. The dyed cloth was subjected to a reduction-rinsing treatment at 85° C. for 10 minutes in a solution of sodium hydroxide (3 parts), hydrosulfite (3 parts) and a betaine amphoteric surfactant (3 parts) in water (3000 parts), washed with water and then dried, thereby obtaining a dyed product having a red color superior in light fastness, sublimation fastness and wet fastness.

EXAMPLE 91

A printing paste was prepared by mixing the compound (1.3 part) represented by the formula (1) obtained in Example 1, ligninsulfonic acid (3.7 parts), hot water (35 parts) and a half emulsion paste (60 parts) having the following composition.

| | |
|---|---|
| O/W emulsion | 300 parts |
| Maypro gum 12% paste | 694 parts |
| Sodium chlorate | 4 parts |
| Tartaric acid | 2 parts |
| | 1,000 parts |

Polyesther cloth (Tetron tropical, a product of Teijin Limited, Japan) was printed with the above obtained printing paste, pre-dried and steamed for 7 minutes at 170° C. under atmospheric pressure. The printed cloth was subjected to a reduction-rinsing treatment, washing with water and softening and anti-static finishings in this order in a manner similar to that of Example 90. The thus obtained product of a red color was found to have superior light, sublimation and wet fastness properties, particularly washing fastness.

We claim:

1. A process for producing benzodifuranone compound of the following formula (I),

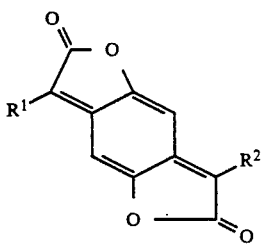
(I)

wherein $R^1$ and $R^2$ are each independently a naphthyl group, an unsubstituted phenyl group or a phenyl group substituted with one or more substituents selected from the group consisting of nitro, halo, alkyl, alkoxyl, phenyl, alkoxyphenyl, phenoxy, hydroxyl, cyano, carbgoxyl, alkoxycarbonyl, phenoxycarbonyl, carbamoyl, sulfo, chlorosulfonyl, alkoxysulfonyl, phenoxysulfonyl, sulfamoyl, mercapto, alkylthio, phenylthio, amino, alkylamino, acylamino, phospho, alkylphosphonyl, phenylphosphonyl, alkylsulfonyl, phenylsulfonyl, formyl, azo and a group represented by the formula (i) or (ii),

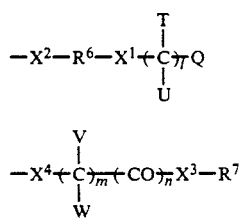
(i)

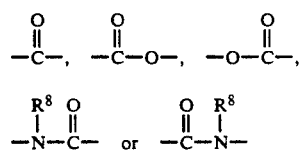
(ii)

wherein $R^6$ is a methylene group or a straight or branched $C_2$-$C_6$ alkylene group which may be substituted by hydroxyl group, an alkoxyl group or an alkylcarbonyloxy group, $X^1$ is a direct linkage or a divalent group of —O—, —S—, —SO—, —SO$_2$—,

in which $R^8$ is a hydrogen atom or an alkyl group,

in which $R^8$ is as defined above, $X^2$ is —O— or

in which $R^8$ is as defined above, T and U are each independently a hydrogen atom or an alkyl group, l is 0 or an integer of 1 to 3, Q is a 5-, 6- or 7-membered saturated or unsaturated heterocyclic ring residue having from 1 to 3 hetero atoms, said hetero atom being selected from the group consisting of nitrogen, sulfur and oxygen, said heterocyclic ring residue being unsubstituted or substituted once or twice by halogen, hydroxy, $C_1$ to $C_4$ alkyl, $C_1$ to $C_4$ alkoxy, $C_1$ to $C_4$ alkylcarbonyl, $C_1$ to $C_4$ alkoxycarbonyl, cyano, or primary, secondary, or tertiary amine which is unsubstituted or substituted by $C_1$ to $C_4$ alkyl or keto, wherein said heterocyclic ring may be condensed with benzene or a 5- or 6-membered heterocylic ring having 1 to 2 hetero atoms selected from the group consisting of nitrogen and sulfur, $R^7$ is an alkyl group, $X^3$ is —O— or —S—, $X^4$ is —— or

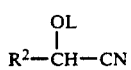

in which $R^8$ is as defined above, U and W are each independently a hydrogen atom or an alkyl group, m is an integer of 1 to 3, n is 0 or 1, provided that m+n is at least 2, which process comprises allowing benzofuran compound of the following formula (II),

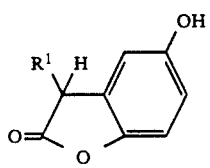
(II)

wherein $R^1$ is as defined above, to react with an acetonitrile compound of the following formula (III), $$R^2-\overset{\overset{\displaystyle OL}{|}}{CH}-CN \quad (III)$$

wherein $R^2$ is as defined above, and L is —COR$^3$, —CO$_2$R$^4$ or —SO$_2$R$^5$ in which $R^3$, $R^4$ and $R^5$ are each independently an alkyl or phenyl group, in the presence of at least one acid catalyst, followed by oxidation in the presence of at least one oxidizing agent.

2. The process according to claim 1, wherein the acid catalyst is used in an amount of at least 0.5 mole per mole of the benzofuran compounds.

3. The process according to claim 1, wherein the reaction between the benzofuran compound of the formula (II) and the acetonitrile compound of the formula (III) is carried out in the presence of a solvent.

4. The process according to claim 3, wherein the solvent is benzene, toluene, xylene, mesitylene, mono-, di- or tri-chlorobenzene, bromobenzene, chloronaphthalene, 1,2-dichloroethane, 1,1,1-trichloroethane, 1,1,2,2-tetrachloroethane, trichloroethylene, tetrachloroethylene, dichloromethane, chloroform, carbon tetrachloride, bromoform, low boiling petroleum fractions, nitrobenzene, nitrotoluene, nitromethane, methylisobutyl ketone, sulfolane, formic acids, acetic acid, propionic acid or acetic anhydride.

5. The process according to claim 4, wherein the solvent is are toluene, monochlorobenzene, dichlorobenzene, 1,2-dichloroethane, 1,1,1-trichloroethane, 1,1,2,2-tetrachloroethane, trichloroethylene, dichloromethane or chloroform.

6. The process according to claim 1, wherein the reaction between the benzofuran compound of the formula (II) and the acetonitrile compound of the formula (III) is carried out at a temperature of 30° to 180° C.

7. The process according to claim 1, wherein the acetonitrile compound of the formula (III) is prepared by allowing an aldehyde compound of the following formula (V), $$R^2—CHO \qquad (V)$$

wherein $R^2$ is as defined in claim 1, to react with a metallic cyanide compound in the presence of an acid halide of the following formula (VI), $$L—Hal \qquad (VI)$$

wherein L is as defined in claim 1, and Hal is a halo group.

8. The process according to claim 1, wherein the oxidizing agent is at least one member selected from chloranil, bromanil, thiosulfate, nitrite, hypochlorite, chlorite, chlorate, perchlorate, persulfate, periodate, perborate, permanganate, vanadate, dichromate, iodine nitrate, tetrachlorohydroquinone, lead dioxide, manganese dioxide, vanadium pentoxide, nitrobenzene, dicyanodichlorobenzoquinone, hydrogen peroxide and air.

9. The process according to claim 8, wherein the oxidizing agent is a mixture of one nitrite with one selected from chloranil, bromanil and dicyanodichlorobenzoquinone.

10. The process according to claim 1, wherein the oxidizing agent is a mixture of chloranil and sodium nitrite.

11. The process according to claim 1, wherein the oxidation is carried out at a temperature of 30° to 180° C.

12. A process according to claim 1, wherein Q is an unsaturated heterocyclic ring residue selected from the group consisting of furyl, thienyl, pyrrolyl, pyridyl, pyranyl, thiazolyl, oxazolyl, imidazolyl, thiadiazolyl, and s-triazinyl.

13. A process according to claim 1, wherein Q is a saturated heterocyclic ring residue selected from the group consisting of tetrahydrofuryl, tetrahyrdothienyl, pyrrolidyl, piperidyl, tetrahydropyranyl, piperazinyl, morpholinyl, thiazanyl, and hexahydroazepinyl.

14. A process according to claim 1, wherein Q is a condensed heterocyclic ring residue selected from the group consisting of benzofuranyl, benzothienyl, indolyl, benzoxazolyl, benzoimidazolyl, benzothiazolyl, thiazolo[4,5-b]pyridynyl, thieno[3,2-b]thienyl, 1,3-dihydro-2H-1,4-benzoxazinyl.

15. A process according to claim 1, wherein Q is a heterocyclic ring unsubstituted or substituted by halogen or methyl.

16. The process according to claim 1, wherein the acid catalyst is benzenesulfonic acid, p-toluenesulfonic acid, benzene-m-disulfonic acid, methanesulfonic acid, trifluoroacetic acid, titanium tetrachloride, aluminum chloride, stannous chloride, stannic chloride, ferrous chloride, ferric chloride, zinc chloride, boron fluoride, sulfuric acid or hydrochloric acid.

* * * * *